US006451207B1

(12) United States Patent
Sterman et al.

(10) Patent No.: US 6,451,207 B1
(45) Date of Patent: Sep. 17, 2002

(54) MAGNETIC CELL SEPARATION DEVICE

(75) Inventors: Martin D. Sterman, Boston, MA (US); Paul Lituri, Milford, NH (US); Richard E. Stelter, Livermore, CA (US)

(73) Assignee: Dexter Magnetic Technologies, Inc., Fremont, CA (US)

( * ) Notice: Subject to any disclaimer, the term of this patent is extended or adjusted under 35 U.S.C. 154(b) by 0 days.

(21) Appl. No.: 08/868,598

(22) Filed: Jun. 4, 1997

(51) Int. Cl.[7] .............................................. G01N 33/553
(52) U.S. Cl. ........................ 210/222; 335/306; 436/526
(58) Field of Search .......................... 210/222; 335/306, 335/304, 302; 209/223.2, 224; 436/177, 526

(56) References Cited

U.S. PATENT DOCUMENTS

| | | | |
|---|---|---|---|
| 3,365,599 A | | 1/1968 | Brzezinski et al. |
| 5,269,915 A | | 12/1993 | Clair |
| 5,466,574 A | | 11/1995 | Liberti et al. |
| 5,622,831 A | | 4/1997 | Liberti et al. |
| 5,797,498 A | * | 8/1998 | Kobayashi et al. |

FOREIGN PATENT DOCUMENTS

| | | |
|---|---|---|
| GB | 1 202 100 | 8/1970 |
| WO | WO 94/15696 | 7/1994 |

OTHER PUBLICATIONS

PCT International Search Report for PCT/US98/11816 (GZ0105PCT).

Wasmuth, H–D, "Benefication of Magnetic Iron Ores and Industrial Minerals by Open Gradient Separation", Aufbereitungs Technik, vol. 35, No. 4, Apr. 1994, pp. 190–194, 196–199.

Ziock, K.P. et al., "One Tesla rare–earth permanent quadrupole magnet for spin separation o fmetal clusters", Review of Scientific Instruments, vol. 58, No. 4, Apr. 1987, pp. 557–562.

* cited by examiner

*Primary Examiner*—Joseph W. Drodge
*Assistant Examiner*—Terry K. Cecil
(74) *Attorney, Agent, or Firm*—Blakely Sokoloff Taylor & Zafman, LLP

(57) ABSTRACT

The magnetic pole device of the present invention has four polar magnets and any number of interpolar magnets adjacent to and in between said polar magnets. The interpolar magnets are positioned to progressively rotate towards the orientation of the four polar magnets. Such a magnetic device would create an even flux within a liquid sample and cause the radial movement of magnetized particles toward the inner wall of the surrounding magnets.

18 Claims, 2 Drawing Sheets

MAGNETIC CELL SEPARATION DEVICE

BACKGROUND OF THE INVENTION

In the field of biology, a technique for efficiently separating one type or class of cell from a complex cell suspension would have wide applications. For example, the ability to remove certain cells from a clinical blood sample that were indicative of a particular disease state could be useful as a diagnostic for that disease.

It has been shown, with limited success, that cells tagged with micron-sized (0.1 μm) magnetic or magnetized particles can be removed or separated from mixtures using magnetic devices that either repel or attract the tagged cells. For the removal of desired cells, i.e., cells which provide valuable information, the desired cell population is magnetized and removed from the complex liquid mixture (positive separation). In an alternative method, the undesirable cells, i.e., cells that may prevent or alter the results of a particular procedure, are magnetized and subsequently removed with a magnetic device (negative separation).

Several magnetic devices exist that can separate micron sized (>0.1 μm) magnetic particles from suspension. Particles of this size do not form a stable colloid and will settle out of the suspension. Smaller, colloidal particles (<0.1 μm) have a larger surface to volume ratio, are subject to random thermal (Brownian) motion, and are present in much greater numbers per unit mass. These properties make it more likely that colloidal particles will find a rare cell population among a much larger population of non-desired cells to allow positive selection. It is also likely that a greater percentage of the a particular population of cells could be labeled and subsequently depleted by these numerous, mobile particles to allow negative selection.

However, smaller magnetic particles present unique problems. The magnetic force of attraction between these smaller particles and the separating magnet is directly related to the size (volume and surface area) of the particle. Small magnetic particles are weak magnets. The magnetic gradient of the separating magnetic device must increase to provide sufficient force to pull the labeled cells toward the device.

A need exists for the development of a magnetic device capable of efficiently separating small magnetic particles from a liquid.

SUMMARY OF THE INVENTION

The magnetic pole device of the present invention has four polar magnets and any number of interpolar magnets adjacent to and in between said polar magnets. The interpolar magnets are positioned to progressively rotate towards the orientation of the four polar magnets. Such a magnetic device creates a high flux density gradient within the liquid sample and causes radial movement of magnetized particles toward the inner wall of the surrounding magnets.

In another aspect, the present invention relates to a method of separating non-magnetized cells from magnetized cells using the magnetic device of the present invention.

DETAILED DESCRIPTION OF THE INVENTION

The magnetic pole device of the present invention has four polar magnets and any number of interpolar magnets adjacent to and in between said polar magnets. The interpolar magnets are positioned to progressively rotate towards the orientation of the four polar magnets to form a cylinder. Such a magnetic device would create an even flux within a liquid sample and cause the efficient radial movement of magnetized particles toward the inner wall of the surrounding magnets.

The phrase "north polar magnet" refers to a magnet positioned so that its north pole is positioned toward the interior of the magnetic device. "South polar magnet" refers to a magnet oriented so that its south pole faces the interior of the device.

The phrase "interpolar magnets" refer to the magnets positioned in between the north polar and south polar magnets and oriented so that an imagined line between the interpolar magnet's north and south poles is approximately perpendicular to the center of the device, i.e. the interpolar magnet vectors are between the unlike interior poles of the polar magnets. Therefore, the polarity of the interpolar magnets is such that like poles abut toward the interior of the device. Superposition of the magnetic fields from all magnets results in a high gradient internal magnetic field. Abutting unlike poles on the exterior of the device results in a low reluctance outer return path with minimal external flux leakage. We believe that an infinite number of interpolar magnets with a progressive rotation of the magnetic vector would be optimum, as might be achieved with an isotropic magnetic material and a special magnetizing fixture. However, single, properly sized, interpolar magnets allow the use of high energy anisotropic magnets for the best performance per unit of cost.

The term "cylinder" as used herein is intended to include what is conventionally understood to mean a cylinder, a tube, a ring, a pipe or a roll and intended to include a cylinder that defines any shape between an octagon (such as would be found with the device depicted in FIG. 1) and a circle. The dimensions (i.e. length and diameter) of the defined cylinder needs to be sufficiently large enough to accommodate the insertion of any test tube containing the liquid sample.

Magnets of the present invention can be constructed of iron, nickel, cobalt and generally rare earth metals such as cerium, praseodymium, neodymium and samarium. Acceptable magnets can be constructed of mixtures of the above listed metals (i.e. alloys) such as samarium cobalt or neodymium iron boron. Ceramic, or any other high coercivity material with intrinsic coercivity greater than the flux density produced by superposition where like magnetic poles abut materials, may be used as well.

Figure 1:
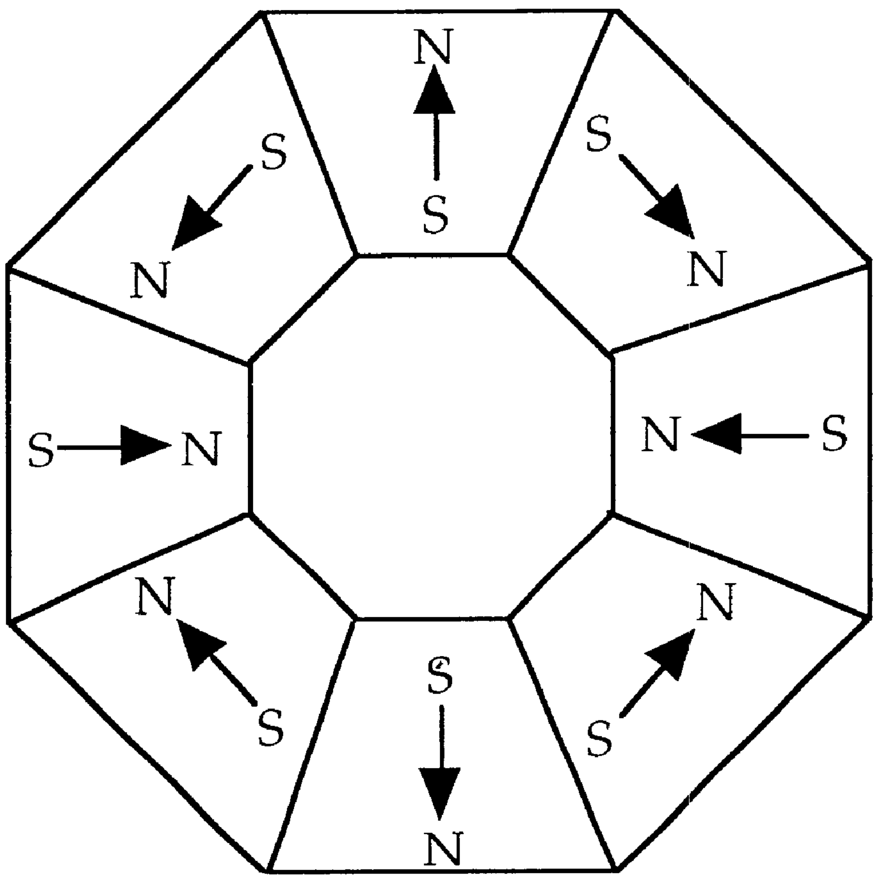
FIG. 1 is an illustration of a top view (cross-section) of one version of the magnetic device of the present invention showing eight adjacent magnet segments with four (4) polar magnets and four (4) interpolar magnets.

In one embodiment of the present invention, the magnetic device comprises eight (8) magnets arranged at 45° intervals. Inward polarity of these magnets are as illustrated in FIG. 1). The magnets with two designations (i.e., N-S, S-N) are arranged such that the poles are perpendicular to the center sample volume. Magnetic flux is directed between the closest opposite poles.

Figure 2:
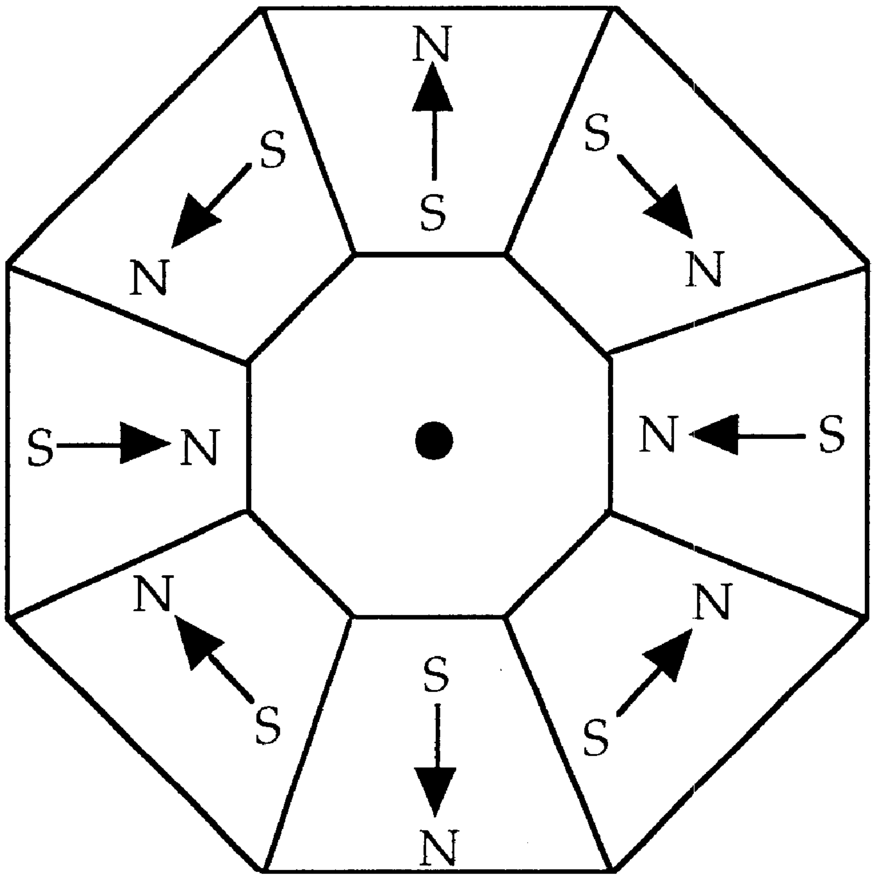
FIG. 2 is an illustration of another embodiment of the present invention showing the top of a rod-shaped magnet that is positioned in the center of the cylindrical space defined by the magnetic device of the present invention.

In another embodiment of the present invention the magnetic device further comprises a rod-shaped magnet that is positioned in the center of the cylindrical space defined by the magnetic device (see FIG. 2). It is believed that such a rod-shaped magnet would contribute to cause the migration of magnetized substances toward the inner walls of the magnetic device of the present invention. The rod-shaped magnet could be attached to the inside of a test tube cap or stopper. The rod-shaped magnet would be inserted into the test tube and the attached test tube cap would seal the top of the test tube. The test tube would be placed into the magnetic device of the present invention for the incubation step to separate the magnetized substances from the non-magnetized substances.

Exemplification

1) Debulking Procedure 21 ml of Percoll (Pharmacia, Piscataway, N.J.) were added to one 50 ml tube with cell trap (Activated Cell Therapies, Mountain View, Calif.). The Percoll was allowed to warm to room temperature. After reaching room temperature, the tube was centrifuged at 850 g (2200 RPM on Sorvall 6000B) for one minute to remove air bubbles.

An overlay of up to 30 ml whole blood were added to the tube and the tube was centrifuged at 850 g (2200 RPM on Sorvall 6000B) for 30 minutes at room temperature. A layer containing peripheral blood mononuclear cells (PMBC) along with other cells appeared in the supernatant above the cell trap. The layer was collected by quickly dumping supernatant into a separate 50 ml polypropylene tube. The volume collected was about 25 ml.

The tube was then centrifuged at 200 g (900–1000 RPM on Sorvall 6000B) for 10 minutes at room temperature. The supernatant was aspirated and the pellet was dispersed with 1 ml of dilution buffer containing 0.5% bovine serum albumin (BSA) (Sigma, St. Louis, Mo.) in phosphate buffered saline (PBS) (BSA/PBS dilution buffer).

The debulked sample was then spiked with fetal liver mononuclear cells (FLMC). FLMC were counted using Hoechst DNA stain, applying the cells on to a filter and counting the stained cells using a microscope equipped with an ultraviolet light.

2) Magnetic Labeling

Mouse anti-CD45 (a leukocyte common antigen) (100 μg/ml) was diluted to 1 μg/ml by adding 2 μl of the antibody to 198 μl of the BSA/PBS dilution buffer. Goat anti-mouse antibody, tagged with magnetic particles purchased from Immunicon (Huntington Valley, Pa.), was diluted from a concentration of 500 μg/ml to 15 μg/ml by adding 30μl of the tagged antibody (ferrofluid) to 970 μl of a dilution buffer provided by Immunicon (ferrofluid dilution buffer).

Resuspended debulked and spiked cells, debulked by the method described above, in 750 μg in the BSA/PBS dilution buffer in 2 ml tube. 200 μl of the diluted mouse anti-CD45 antibody was added to the resuspended cells. The cells and antibody were incubated at room temperature for 15 minutes.

After the 15 minute incubation, 1 ml of the goat anti-mouse ferrofluid was added to the cells and allowed to incubate for an additional 5 minutes at room temperature.

3) Depletion

A 2 ml tube for each sample was placed into two magnetic devices, one being an eight (8) poled magnetic device shown in FIG. 2 and one purchased from Immunicon (a four-poled magnetic device) and allowed to separate for 5 minutes at room temperature.

After the 5 minutes, a Pasteur pipette was used to remove a sample from the top center of the tube. The sample was transferred to a new 2 ml tube. The transferred cells were then centrifuged at 3500 RPM for 3 minutes and resuspended in the BSA/PBS dilution buffer in a volume as shown in the Table.

TABLE

| | Volume (ml) | Starting PMBC | Starting FLMC | Depletion Efficiency | FLMC Recovery |
|---|---|---|---|---|---|
| Immunicon | 1.5 | 3.5E+07 | 236 | 97.40% | 74% |
| quadrapole | 1.5 | 3.5E+07 | 236 | 90.20% | 62% |
| Genzyme | 2.0 | 4.0E+07 | 208 | 98.81% | 90% |
| | 2 | 4.0E+07 | 208 | 98.76% | 101% |
| | 2.0 | 4.0E+07 | 208 | 98.85% | 95% |
| | 1.95 | 5.0E+07 | 408 | 99.08% | 87% |

Depletion efficiency (DE) was determined as follows:

PBMC post-depletion/Starting PBMC×100=X; and 100−X=DE

FLMC recovery (FR) was determined as follows:

Starting FMLC×%FLMC cells not positive for CD45=corrected starting

FMLCs;

and FLMC post-depletion/corrected starting cells×100=FR

It is believed that a magnetic cell separation device with more interpolar magnets would perform better than the device used in the experiments above (i.e. a device using four (4) interpolar magnets as illustrated in FIG. 1).

Equivalents

Those skilled in the art will recognize, or be able to ascertain, using no more than routine experimentation many equivalents to the specific embodiments of the invention described herein. Such equivalents are intended to be encompassed by the following claims.

The invention claimed is:

1. A magnetic device for separating a magnetized substance from a non-magnetized substance suspended in a solution of a container, comprising (a) a first and a second north polar magnet;

(b) a first and a second south polar magnet; and (c) a first, a second, a third and a fourth interpolar magnet; wherein the first north polar magnet is adjacent to the first interpolar magnet, which is adjacent to the first south polar magnet, which is adjacent to the second interpolar magnet, which is adjacent to the second north polar magnet, which is adjacent to the third interpolar magnet, which is adjacent to the second south polar magnet, which is adjacent to the fourth interpolar magnet, which is adjacent to the first north polar magnet.

2. The magnetic device of claim 1, wherein the magnets are constructed of material selected from the group consisting of samarium cobalt, neodymium iron boron, and ceramics.

3. The magnetic device of claim 1, wherein there are two first interpolar magnets, two second interpolar magnets, two third interpolar magnets and two fourth interpolar magnets.

4. The magnetic device of claim 1, wherein the magnetic device defines a cylindrical space and further comprises a rod-shaped magnet positioned in the center of the cylindrical space.

5. A magnet arrangement to separate magnetic particles comprising:

a first magnet and a second magnet to generate north-south magnetic fields, each north-south magnetic field directed substantially away from each other, in a plane co-planar with a horizontal cross-sectional plane of a container therebetween;

a third magnet and a fourth magnet, substantially perpendicular to the first magnet and the second magnet, to generate north-south magnetic fields directed substantially toward each other, in the plane co-planer with the horizontal cross-sectional plane of the container; and a fifth magnet in between the first and the third magnet to generate a north-south magnetic field directed away from the first magnet toward the third magnet, in a plane co-planar with the horizontal cross-sectional plane of the container.

6. The magnet arrangement of claim 5 further comprising a sixth magnet in between the first and the fourth magnet to generate a north-south magnetic field directed away from the first magnet toward the fourth magnet, in a plane co-planar with the horizontal cross-sectional plane of the container.

7. The magnet arrangement of claim 6 further comprising a seventh magnet in between the second and the third magnet to generate a north-south magnetic field directed away from the second magnet toward the third magnet, in a plane co-planar with the horizontal cross-sectional plane of the container.

8. The magnet arrangement of claim 7 further comprising an eighth magnet in between the second and the fourth magnet to generate a north-south magnetic field directed away from the second magnet toward the fourth magnet, in a plane co-planar with the horizontal cross-sectional plane of the container.

9. The magnet arrangement of claim 5 wherein the magnets extend for substantially the length of the container.

10. The magnet arrangement of claim 5 wherein the horizontal cross-sectional plane of the container is substantially concentric with a horizontal cross-sectional plane of the magnet arrangement.

11. The magnet arrangement of claim 5 wherein a magnet is placed at the center of the container.

12. The magnet arrangement of claim 5 wherein a magnet is suspended at the center of the container.

13. The magnet arrangement of claim 5 wherein the magnets are constructed of a material comprising at least one of samarium cobalt, neodymium iron boron, and ceramics.

14. The magnet arrangement of claim 5 wherein the container is any one of a test tube, a beaker, a dish, and a tube.

15. The magnet arrangement of claim 5 wherein the magnets are permanent magnets.

16. The magnet arrangement of claim 5 wherein the magnet particles are biological particles.

17. The magnet arrangement of claim 5 wherein the container contains a plurality of magnetic beads.

18. The magnet arrangement of claim 5 wherein the magnets are substantially trapezoid shaped.

* * * * *